United States Patent [19]
Voss et al.

[11] Patent Number: 5,221,443
[45] Date of Patent: Jun. 22, 1993

[54] LIBERATION OF ORGANIC SULFONIC ACIDS

[75] Inventors: Hartwig Voss, Frankenthal; Rolf Schneider, Mannheim, both of Fed. Rep. of Germany

[73] Assignee: BASF Aktiengesellschaft, Ludwigshafen, Fed. Rep. of Germany

[21] Appl. No.: 795,919

[22] Filed: Nov. 20, 1991

[30] Foreign Application Priority Data

Dec. 22, 1990 [DE] Fed. Rep. of Germany ....... 4041571

[51] Int. Cl.$^5$ ............................................. B01D 61/00
[52] U.S. Cl. ................................. 204/131; 204/182.4; 204/72
[58] Field of Search .................... 204/131, 182.4, 72

[56] References Cited

U.S. PATENT DOCUMENTS

| | | | |
|---|---|---|---|
| 2,693,489 | 11/1954 | Kleinschmidt | 260/513 |
| 2,727,057 | 12/1955 | Park | 260/456 |
| 2,793,229 | 11/1957 | Blaser et al. | 260/513 |
| 2,810,747 | 10/1957 | Sexton et al. | 260/513 |
| 2,818,426 | 12/1957 | Kosmin et al. | 260/481 |
| 2,829,095 | 4/1958 | Oda et al. | 204/98 |
| 3,269,927 | 8/1966 | Bost | 204/131 |
| 3,310,481 | 3/1967 | Mock et al. | 204/182.4 |
| 4,057,481 | 12/1977 | Lee et al. | 204/296 |
| 4,499,028 | 2/1985 | Longley | 260/513 R |
| 4,615,780 | 10/1986 | Walker | 204/182.4 |
| 4,670,125 | 6/1987 | Mueller et al. | 204/296 |
| 4,696,773 | 9/1987 | Lukenbach et al. | 260/513 R |
| 4,781,809 | 11/1988 | Falcone | 204/182.4 |

FOREIGN PATENT DOCUMENTS

| | | |
|---|---|---|
| 960196 | 3/1957 | Fed. Rep. of Germany. |
| 2646421A | 11/1990 | France. |
| 89/01059 | 2/1989 | World Int. Prop. O.. |

OTHER PUBLICATIONS

Ullmanns Encyklopadie der technischen Chemie, 4th Ed., vol. 7, (1979) pp. 199-202.
Ullmanns Encyclopedia of Industrial Chemistry, vol. A3, (1985) pp. 507-537.
Chem. Abstracts, vol. 71, No. 12; Abstract No. 56451F.
Chem. Ing. Tech. 61, 428 (1989).
Chem. Abstracts, vol. 109, No. 16; Abstract No. 131270e.
JP-A 63293189 (Derwent Abstract); Nov. 1988.
JP-A 1304190; Dec. 1989.

*Primary Examiner*—John Niebling
*Assistant Examiner*—Arun S. Phasge
*Attorney, Agent, or Firm*—John H. Shurtleff

[57] ABSTRACT

Organic sulfonic acids are liberated from aqueous solutions of their salts by a process in which the aqueous organosulfonate solution is subjected to electrodialysis with the aid of an electrodialysis cell which consists of diluate chambers DC, acid chambers AC and base chambers BC according to the sequence I $$(MB/AC/MA/DC/MK/BC)_n \qquad I$$

where MB is a bipolar ion exchange membrane, MA is an anion exchange membrane, MK is a cation exchange membrane and n is a number from 1 to 500.

10 Claims, No Drawings

LIBERATION OF ORGANIC SULFONIC ACIDS

In virtually all industrial processes for the preparation of organic sulfonic acids, the latter are obtained in the form of their aqueous salt solutions, i.e., as sulfonates, for example as alkali metal or ammonium-sulfonates (cf. for example U.S. application Ser. No. 2 818 426, DE-A 960 196, U.S. application Ser. No. 2 727 057, U.S. application Ser. No. 2 693 489 and U.S. application Ser. No. 2 810 747). Very expensive chemical processes have been required to date for isolating the free sulfonic acids, for example passing anhydrous hydrogen chloride gas into alcoholic alkali metal sulfonate solutions to precipitate the relevant alkali metal chloride, which is then filtered off from the liberated sulfonic acid (cf. for example U.S. application Ser. No. 4 499 028 and U.S. application Ser. No. 4 696 773). Owing to these expensive isolation processes, the free organic sulfonic acids are generally considerably more expensive than their salts.

It is an object of the present invention to provide a process which is feasible on an industrial scale and makes it possible to liberate organic sulfonic acids in an economical manner from their aqueous salt solutions and either reduce or, preferably, completely avoid the large amounts of waste salts which are produced in conventional isolation processes. The process for liberating the sulfonic acids should, if possible, also achieve an additional purification effect for the particular sulfonic acid to be liberated, i.e., the concentration of any impurities present in the sulfonate salt used should also be decreased in the course of liberating said sulfonic acid.

We have found that this object is achieved by a process for liberating organic sulfonic acids from aqueous solutions of their salts, wherein the aqueous organosulfonate solution is subjected to electrodialysis with the aid of an electrodialysis cell which consists of diluate chambers DC, acid chambers AC and base chambers BC according to sequence I $$(MB/AC/MA/DC/MK/BC)_n \qquad I$$

where MB is a bipolar ion exchange membrane, MA is an anion exchange membrane, MK is a cation exchange membrane and n is a number from 1 to 500.

In the novel process, the organic sulfonic acid is liberated from the aqueous solution of its salts, preferably from the aqueous solution of one of its salts, with the aid of a three-loop electrodialysis process. This procedure involves passing the aqueous sulfonate solution through the diluate chambers DC, water or a dilute solution of the organic sulfonic acid to be liberated through the acid chambers AC and water or a dilute solution of the base corresponding to the cation present in the salt through the base chambers BC of an electrodialysis cell having the sequence I $$(MB/AC/MA/DC/MK/BC)_n \qquad I$$

where MB, MA, MK, AC, BC and DC have the abovementioned meanings and n is an integer of from 1 to 500, preferably from 1 to 300, particularly preferably from 50 to 300, and carrying out the electrodialysis using a current density of from 1 to 500, preferably from 1 to 300, particularly preferably from 1 to 100, mA/cm$^2$, the electric field required for this purpose being applied by means of two electrodes at the ends of the membrane stack. The membrane stack is advantageously separated from the two electrode compartments, the cathode compartment and the anode compartment, by an additional ion exchange membrane in each case, preferably a cation or anion exchange membrane During operation of the electrodialysis cell, the two electrode compartments are continuously flushed with an electrode flushing solution, for example a solution of sulfuric acid or, preferably, a solution of the base to be liberated or of the relevant sulfonic acid. In selecting the material of the ion exchange membranes separating the electrode compartments from the membrane stack, it is of course necessary to ensure that this material is chemically stable to the electrode flushing solution used in each case.

During electrodialysis of the organic sulfonate solution in the electrodialysis cell described above, the following processes take place (schematic representation):

Owing to the electric field applied at the membrane stack, the organosulfonate anion and the relevant counter-cation migrate from the organosulfonate solution fed into the diluate chambers DC and move toward the anode or cathode, respectively, the anion entering the acid chamber AC after passing through the anion exchange membrane MA and the cation entering the base chamber BC after passing through the cation exchange membrane MK. In this process, electrically neutral impurities of the organosulfonate solution which are dissolved in the diluate remain behind in the diluate chamber. During this procedure, water is, expressed purely formally, decomposed into protons and hydroxyl anions in the bipolar membrane MB under the action of the applied electric field, after which the protons on the way to the cathode migrate into the acid chambers AC and the hydroxyl anions on the way to the anode migrate into the base chambers BC, where they combine with the organosulfonate anions which have migrated there or with the relevant counter-cations to form the free organosulfonic acid or the free base. The organosulfonic acids and of course also the relevant bases can be obtained, as such or in the form of solutions of the desired concentration, depending on requirements, from the organosulfonic acid or base solutions formed in this way in the acid and base chambers, by a conventional method, for example by evaporation of the water and, if necessary, subsequent crystallization.

With the aid of the novel process, virtually all organosulfonic acids can be liberated from their salts, provided that the organosulfonate anions and the relevant counter-cations are capable, under the electrodialysis conditions employed, of penetrating the anion or cation exchange membranes used. This ability is dependent on the one hand on the permeability of the relevant membranes and on the other hand on the structure and in particular on the molecular size of the relevant organosulfonate anions and of the counter-cations. Usually, organosulfonic acids having molecular weights of up to about 200 Dalton can be liberated from their salts with the aid of the novel process. The same is also roughly true for the relevant counter-cations.

The organosulfonic acids liberated by the novel process may be aliphatic, cycloaliphatic, aromatic or araliphatic and may carry substituents which are inert under the electrodialysis conditions, such as halogen atoms or hydroxyl or ether groups. The novel process is of course also suitable for liberating unsaturated, aliphatic sulfonic acids. For example, the following sulfonic acids can be liberated from their salts by the novel process: benzenesulfonic acid, p-toluenesulfonic acid, benzylsulfonic acid, 3-oxopropane-1-sulfonic acid, 4-hydroxybutane-2-sulfonic acid, 3-hydroxybutane-1-sulfonic acid, 2-hydroxyethane-1-sulfonic acid, 2-hydroxypropane-1-sulfonic acid, 2-hydroxybut-3-ene-1-sulfonic acid, vinylsulfonic acid, 3-hydroxypropane-1,2-disulfonic acid, methanesulfonic acid, ethanesulfonic acid, trifluoromethanesulfonic acid, methanedisulfonic acid, 2-chloroethane-1-sulfonic acid, allylsulfonic acid and prop-2-yne-sulfonic acid.

Examples of bases which can be liberated are alkali metal hydroxides, quaternary ammonium hydroxides, tertiary, secondary and primary amines and ammonia.

Ion exchange membranes which may be used are conventional, commercial ion exchange membranes which have, for example, a thickness of from 0.1 to 1 mm and a pore diameter of from 1 to 30 μm or a gel-like structure. The anion exchange membranes are usually composed of a matrix polymer, for example a polystyrene/divinylbenzene resin which contains chemically bonded, cationic groups, for example ammonium, alkylammonium or dialkylammonium groups, whereas in the case of the cation exchange membranes the matrix polymer carries chemically bonded, anionic groups, for example carboxylate and sulfonate groups. Ion exchange membranes of the stated type are commercially available, for example under the names SELEMION ® (Asahi Glass), NEOSEPTA ® (Tokoyama Soda) or IONAC ® (Ionac Chemical Company). The bipolar membranes have an asymmetric structure and carry anionic groups on one side of the membrane and cationic groups on the other side. The bipolar membranes can be produced, for example, by placing together, adhesively bonding or connecting the cation and anion exchange membranes, for example by the processes described in EP-A 193 959 and WO 89/01059, or as a single-film membrane, as described in, for example, U.S. application Ser. No. 4 057 481.

The electrodialysis cells used in the novel process are conventional apparatuses which are equipped with exchange membranes and sealing frames and have up to 1,500, preferably up to 900, chambers arranged parallel to one another, corresponding to 500 or 300 sequences. The membrane spacings are usually from 0.4 to 2 mm.

The novel process can be carried out both batchwise and continuously and is as a rule operated at from 0° to 100° C., preferably from 10° to 60° C., and at from 1 to 10 bar, preferably at atmospheric pressure. The flow rate of the solutions passed through the diluate, acid and base chambers is in general set at a rate of from 0.001 to 2.0, preferably from 0.01 to 0.1, m/s.

The organosulfonate solutions used in the novel process usually have a concentration of from 0.1 to 4, preferably from 0.5 to 2, mol of sulfonate/l. Organosulfonic acid solutions having a sulfonic acid content of up to 3 mol of sulfonic acid/kg of solution can be obtained with the aid of the present process. Similarly, base solutions having a base concentration of up to 3 mol of base/kg of solution can be obtained in the base chambers in the novel process. In producing such concentrated base solutions, it is possible that an amine liberated in the case of the electrodialytic cleavage of an ammonium organosulfonate will be deposited as an organic phase in the base chamber owing to the solubility limit being exceeded.

However, the sulfonic acid solutions obtainable by the novel process, including the base solutions, are generally obtained in very pure form since any electrically neutral impurities present in the sulfonate used are either completely separated off or at least greatly reduced in concentration in the course of liberation of the sulfonic acids and bases. Thus, not only is the novel process advantageous for liberating and additionally purifying the sulfonic acids, it also gives very pure base solutions which have many intended uses.

Organic sulfonic acids have a broad spectrum of applications, for example as an acid for reducing the pH and as acidic catalysts, and furthermore as intermediates for the synthesis of drugs and of dyes. In this context, reference may be made, by way of example, to Ullmanns Encyklopädie der technischen Chemie, 4th Edition, Volume 7, pages 199–202, Verlag Chemie, Weinheim 1979, and Ullmann's Encyclopedia of Industrial Chemistry, Vol. A3, pages 507–537, VCH Verlagsgesellschaft, Weinheim 1985.

EXAMPLES

General electrodialysis conditions:

A laboratory electrodialysis cell having the following structure was used:

KA/(sequence I)$_{n-2}$/MB/KK

KA: Anode chamber with integral anode

KK: Cathode chamber with integral cathode.

The effective area of a membrane was 3.14 cm$^2$ and the membrane spacing was 1 cm. The chambers AC, DC and BC had separate pump circulations, and chambers KK and KA were connected to one another by a common pump circulation. The process was carried out at from 35° to 38° C. The temperature was adjusted by means of heat exchangers integrated in the pump circulations. Electrodialyses were carried out batchwise and with a constant current of 300 mA.

During the electrodialyses, organosulfonate solutions contaminated with electrically neutral, organic substances were passed through the diluate chambers DC in some cases and pure organosulfonate solutions in other cases. Water or a dilute solution of the particular sulfonic acid or base to be liberated was fed into the acid chambers AC and the base chambers BC. Either dilute sodium hydroxide solution or dilute sodium sulfate solution was pumped through the electrode compartments KA and KK.

The cation or anion exchange membranes SELEMION ® CMV or AMV (Asahi Glass) were used. The bipolar membranes were produced from monopolar membranes by the process of U.S. application Ser. No. 4670125.

EXAMPLE 1

An aqueous sodium 2-hydroxyethanesulfonate solution which had been prepared by reacting equimolar amounts of ethylene oxide with a 40% strength by weight sodium bisulfite solution at 40° C. in an autoclave and contained ethylene glycol as an impurity was subjected to electrodialysis according to the general electrodialysis conditions. Before being fed into the electrodialysis apparatus, the 49% strength by weight sulfonate solution was diluted with water in a ratio of 1 : 1 (v/v). The electrodialysis time was 14 h and a 5% strength by weight sodium sulfate solution was used as the electrode flushing solution. The results of this electrodialysis are listed in Table 1.

TABLE 1

|  | Used | | | Discharged | | |
| --- | --- | --- | --- | --- | --- | --- |
|  | Base loop | Acid loop | Diluate loop | Base loop | Acid loop | Diluate loop |
| Amount (g) | 130 | 144 | 100 | 155 | 183 | 34 |
| $RSO_3Na$ (mol/kg) | — | — | 1.80 | — | — | 0.059 |
| $RSO_3H$ (mol/kg) | — | — | — | — | 0.94 | — |
| NaOH (mol/kg) | 0.03 | — | — | 1.16 | — | — |
| Ethylene glycol (% by wt.) | — | — | 0.2 | — | — | 0.5 |

EXAMPLE 2

A pure sodium methanesulfonate solution was subjected to electrodialysis according to the general electrodialysis conditions in the course of 25.33 h. The concentrations used and discharged in this electrodialysis are shown in Table 2. A 1.2% strength by weight sodium hydroxide solution was used as the electrode flushing solution.

TABLE 2

|  | Used | | | Discharged | | |
| --- | --- | --- | --- | --- | --- | --- |
|  | Base loop | Acid loop | Diluate loop | Base loop | Acid loop | Diluate loop |
| Amount (g) | 106.6 | 183.3 | 179.5 | 155.2 | 245.4 | 64.0 |
| $CH_3SO_3Na$ (mol/kg) | — | — | 1.91 | 0.009 | 0.01 | 0.001 |
| $CH_3SO_3H$ (mol/kg) | — | 0.014 | — | — | 1.39 | — |
| NaOH (mol/kg) | 0.12 | — | — | 2.21 | — | — |

EXAMPLE 3

In the electrodialysis of a waste sodium methanesulfonate solution, carried out according to the general electrodialysis conditions, the results shown in Table 3 were obtained. The sodium methanesulfonate solution used had been obtained by reacting an ammonium methanesulfonate solution with sodium hydroxide solution and stripping the ammonia liberated. The ammonium methanesulfonate solution in turn had been formed in the synthesis of a polyetherdiamine from the corresponding polyether bismethanesulfonate by reacting the latter with ammonia and contained the relevant polyetherdiamine as an impurity.

The electrodialysis time in this experiment was 24 h, and a 1.1% strength by weight sodium hydroxide solution was used as the electrode flushing solution.

TABLE 3

|  | Used | | | Discharged | | |
| --- | --- | --- | --- | --- | --- | --- |
|  | Base loop | Acid loop | Diluate loop | Base loop | Acid loop | Diluate loop |
| Amount (g) | 103.3 | 286.3 | 192.5 | 156.5 | 339.5 | 81.7 |
| $CH_3SO_3Na$ (mol/kg) | — | — | 1.64 | — | — | 0.05 |
| $CH_3SO_3H$ (mol/kg) | — | 0.06 | — | — | 0.94 | — |
| NaOH (mol/kg) | 0.11 | — | 0.24 | 2.3 | — | — |
| Polyetherdiamine (% by wt.) | — | — | 3.3 | — | — | 7.6 |

EXAMPLE 4

An aqueous solution of a mixture of the sodium salts of 2-hydroxybut-3-ene-1-sulfonic acid and 1-hydroxybut-3-ene-2-sulfonic acid was subjected to electrodialysis according to the general electrodialysis conditions. This sulfonate solution had been formed in the reaction of vinyloxirane with sodium bisulfite solution by a process similar to that described in Example 1. The concentrations used and discharged are shown in Table 4. The electrodialysis time in this experiment was 19 h, and a 1% strength by weight sodium hydroxide solution was used as the electrode flushing solution.

TABLE 4

|  | Used | | | Discharged | | |
| --- | --- | --- | --- | --- | --- | --- |
|  | Base loop | Acid loop | Diluate loop | Base loop | Acid loop | Diluate loop |
| Amount (g) | 205.2 | 221.4 | 150.0 | 235.4 | 292.3 | 49.3 |
| $RSO_3Na$ (mol/kg) | — | — | 1.72 | — | — | 0.08 |
| $RSO_3H$ (mol/kg) | — | — | — | — | 0.85 | — |
| NaOH (mol/kg) | 0.15 | — | — | 1.19 | — | — |

We claim:

1. A process for liberating an organic sulfonic acid which has a molecular weight of up to about 200 Dalton from an aqueous solution of an organosulfonate salt which comprises:

subjecting the aqueous solution containing said organosulfonate salt in a concentration of about 0.1 to 4 mol/l to electrodialysis at a temperature of 0-100° C., under a pressure of 1-10 bar and with an applied electrical field at a current density of 1-500 $mA/cm^2$, by passing said solution through an electrodialysis cell consisting of diluate chambers DC, acid chambers AC and base chambers BC according to the sequence I $$(MB/AC/MA/DC/MK/BC)_n \qquad I$$

where MB is a bipolar membrane, MA is an anion exchange membrane, MK is a cation exchange membrane and n is a number from 1 to 500, the initial aqueous solution being fed through the diluate chambers, water or a dilute solution of the organic sulfonic acid obtained from the sulfonate being fed through the acid chambers and water or a dilute solution of the base obtained from the sulfonate being fed through the base chambers, such that under the applied electrical field, the organosulfonate anion migrates through the anion exchange membrane toward the bipolar membrane on the cathode side of the cell to form the organic sulfonic acid product liberated from the salt.

2. A process as claimed in claim 1, wherein the cation of the organosulfonate salt migrates through the cation exchange membrane toward a bipolar membrane on the anode side of the cell to form the base product liberated from the salt.

3. A process as claimed in claim 2, wherein said base product also has a molecular weight of up to about 200 Dalton.

4. A process as claimed in claim 1, wherein the temperature is about 10° to 60° C.

5. A process as claimed in claim 1, wherein the pressure is atmospheric.

6. A process as claimed in claim 1, wherein the current density is about 1 to 100 mA/cm$^3$.

7. A process as claimed in claim 1, wherein n in the sequence I is from 1 to 300.

8. A process as claimed in claim 1, wherein n in the sequence I is from about 50 to 300.

9. A process as claimed in claim 1, wherein the initial organosulfonate solution has a concentration of about 0.5 to 2 mol/l.

10. A process as claimed in claim 1, wherein the initial organosulfonate solution contains electrically neutral organic impurities which are substantially retained in the diluate chambers of said sequence I.

* * * * *